(12) United States Patent
Phillips et al.

(10) Patent No.: US 7,486,084 B2
(45) Date of Patent: Feb. 3, 2009

(54) APPARATUS AND METHOD FOR IDENTIFYING THE PRESENCE OF HIGH CONDUCTIVITY OR PERMITTIVITY CONDITIONS IN ELECTRICALLY INSULATING MATERIALS

(75) Inventors: Andrew John Phillips, Harrisburg, NC (US); Gordon Luke van der Zel, Huntersville, NC (US)

(73) Assignee: Electric Power Research Institute, Inc., Charlotte, NC (US)

( * ) Notice: Subject to any disclaimer, the term of this patent is extended or adjusted under 35 U.S.C. 154(b) by 143 days.

(21) Appl. No.: 11/554,069

(22) Filed: Oct. 30, 2006

(65) Prior Publication Data

US 2008/0100299 A1    May 1, 2008

(51) Int. Cl.
*G01N 27/62* (2006.01)
*H01H 31/12* (2006.01)
(52) U.S. Cl. ...................... 324/551; 324/464
(58) Field of Classification Search ............... 324/551, 324/464
See application file for complete search history.

(56) References Cited

U.S. PATENT DOCUMENTS 5,254,954 A * 10/1993 Fujimoto et al. ............ 324/551
6,977,509 B2 * 12/2005 Carroll et al. ............... 324/544

FOREIGN PATENT DOCUMENTS

| GB | 1212534 | 11/1970 |
| WO | 95/05311 A1 | 5/1990 |
| WO | 95/23326 A1 | 8/1995 |

* cited by examiner

*Primary Examiner*—Vincent Q Nguyen
*Assistant Examiner*—Amy He
(74) *Attorney, Agent, or Firm*—Trego, Hines & Ladenheim, PLLC

(57) ABSTRACT

An apparatus and method for detecting the presence of high conductivity or permittivity conditions in electrically insulating materials, including a first electrode and a second electrode for being placed in spaced-apart relation on an insulator to be tested for a high conductivity or permittivity condition, and a high voltage source for energizing the first electrode and second electrode at different potentials. At least one gas gap is positioned between the first electrode and the second electrode and proximate a surface of the insulator; and a detector determines the level of ionization of the at least one gas gap while the electrodes are energized.

16 Claims, 3 Drawing Sheets

APPARATUS AND METHOD FOR IDENTIFYING THE PRESENCE OF HIGH CONDUCTIVITY OR PERMITTIVITY CONDITIONS IN ELECTRICALLY INSULATING MATERIALS

TECHNICAL FIELD AND BACKGROUND OF THE INVENTION

This invention relates to a detector for identifying the presence of high conductivity or permittivity conditions in electrically insulating materials and related method. A requirement for ensuring worker safety when performing live work (LW) with polymer insulators (also called composite or non-ceramic insulators (NCI)), is to confirm the short-term (i.e. for the duration of the work) electrical and mechanical integrity of both the installed and the replacement polymer units. Currently there are no generally accepted and easily applied procedures to accomplish this. Consequently some utilities have opted not to use polymer insulators. In addition, a number of utilities that do use polymer insulators avoid live work on structures on which these insulators have been installed.

Although both the electrical and mechanical integrity of the insulator are a concern, often work practices can be implemented to address the mechanical concerns. The focus therefore of this application is to provide a simple detector to assess the electrical integrity of a polymer insulator and that can also be used for a wide range of other insulating components.

The detector disclosed in this application has the capacity to identify conductive, semi-conductive or high permittivity conditions, both internal and external without likely physical contact with internal conductive defects. The detector is able to identify conductive, semi-conductive and high permittivity internal conditions which occur in service—and are small in dimension electrically.

The detector is portable, lightweight, able to be used on energized installed insulators, and provides a simple "Go/No Go" output. As noted above, the detector is not only be applicable to polymer insulators, but also to other insulating components such as fiberglass hot sticks, guy strain insulators, fiberglass cross-arms, composite poles, and the like. Thus, the technology incorporated in the detector does not necessarily need to be utilized to evaluate components that fill an electrical function—rather it is applicable to any component which is manufactured from a material having insulating properties and the internal or external condition being sought is conductive, semi-conductive or has a high permittivity.

SUMMARY OF THE INVENTION

Therefore, it is an object of the invention to provide a detector that meets the conditions and has the characteristics described above. These and other objects of the invention are achieved by providing an apparatus for detecting the presence of high conductivity or permittivity conditions in electrically insulating materials, comprising a first electrode and a second electrode for being placed in spaced-apart relation on an insulator to be tested for a high conductivity or permittivity condition, and a high voltage source for energizing the first electrode and second electrode at different potentials. At least one gas gap is positioned between the first electrode and the second electrode and proximate to a surface of the insulator; and a detector determines the level of ionization of the at least one gas gap while the electrodes are energized.

According to another embodiment of the invention, the high voltage source is selected from the group of high voltage sources consisting of a high frequency, high voltage source, a direct current source and a power frequency source.

According to another embodiment of the invention, a pair of closely spaced-apart gas gaps are positioned on the insulator.

According to another embodiment of the invention, the first electrode and second electrode each comprise plates with respective major surfaces for being positioned generally perpendicular to a longitudinal axis of the insulator being tested.

According to another embodiment of the invention, a detector module is provided having a receiver for receiving data indicative of the level of ionization from the detector and a transmitter for transmitting the data to an electronic circuit for data analysis.

According to another embodiment of the invention, the detector comprises an optical detector for transmitting an optical signal to the receiver of the detector module.

According to another embodiment of the invention, a RF transmitter is provided for transmitting data indicative of the level of ionization of the at least one gas gap while the electrodes are energized to a RF receiver, and an electronic circuit is provided for analyzing the data and comparing the data against a predetermined threshold level and providing an output value.

According to another embodiment of the invention, an apparatus is provided for detecting the presence of high conductivity or permittivity conditions in electrically insulating materials, and comprises a first electrode plate and a second electrode plate for being placed in spaced-apart relation on an insulator to be tested for a high conductivity or permittivity condition, and a HF HV source for energizing the first electrode and second electrode at different potentials. First and second gas gaps are positioned in spaced-apart relation between the first electrode and the second electrode on a surface of the insulator, and an optical detector determines the level of ionization of the first and second gas gaps while the electrodes are energized. A detector module having a receiver is provided for receiving data indicative of the level of ionization from the detector and a transmitter transmits the data to electronic circuit for data analysis. The detector comprises an optical detector for transmitting an optical signal to the receiver of the detector module, and a RF transmitter transmits data indicative of the level of ionization of the first and second gas gaps. An electronic circuit analyzes the data, compares the data against a predetermined threshold level and provides an output value.

According to another embodiment of the invention, a method is provided for detecting the presence of high conductivity or permittivity conditions in electrically insulating materials, and comprising the steps of positioning a first electrode and a second electrode in spaced-apart relation to an insulator to be tested for a high conductivity or permittivity condition, positioning at least one gas gap between the first electrode and the second electrode and proximate to a surface of the insulator; energizing the first electrode and second electrode with a high voltage source at different potentials, and detecting the level of ionization of the at least one gas gap while the electrodes are energized.

According to another embodiment of the invention, the method of energizing the first and second electrodes with the high voltage source comprises the step of applying a high voltage from the group of high voltage sources consisting of a high frequency, high voltage source, a direct current source and a power frequency source.

According to another embodiment of the invention, the method includes the step of positioning a pair of closely spaced-apart gas gaps between the first electrode and the second electrode.

According to another embodiment of the invention, wherein the first and second electrodes each include plates having opposed major surfaces, and the method includes the step of positioning the first and second electrode plates with their respective major surfaces generally perpendicular to a longitudinal axis of the insulator being tested.

According to another embodiment of the invention, the method includes the step of receiving data indicative of the level of ionization from the detector and transmitting the data to an electronic circuit for data analysis.

According to another embodiment of the invention, the step of detecting the level of ionization comprises detecting light indicative of the level of ionization with an optical detector and transmitting the optical signal to a receiver.

According to another embodiment of the invention, the method includes the steps of providing a RF transmitter for transmitting data indicative of the level of ionization of the at least one gas gap while the electrodes are energized to a RF receiver, and utilizing an electronic circuit for analyzing the data and comparing the data against a predetermined threshold level and providing an output value.

According to another embodiment of the invention, a method is provided for detecting the presence of high conductivity or permittivity conditions in electrically insulating materials, and comprises the steps of providing a first electrode plate and a second electrode plate for being placed in spaced-apart relation on an insulator to be tested for a high conductivity or permittivity condition, and providing a HF HV source for energizing the first electrode and second electrode at different potentials. First and second gas gaps are positioned in spaced-apart relation between the first electrode and the second electrode proximate a surface of the insulator, and the first electrode and second electrodes are energized at different potentials. An optical detector is used to determine the level of ionization of the first and second gas gaps while the electrodes are energized, and data indicative of the level of ionization is detected and transmitted to an electronic circuit for data analysis. The data is analyzed and compared against a predetermined threshold level and providing an output value.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED
EMBODIMENT AND BEST MODE

Figure 1:
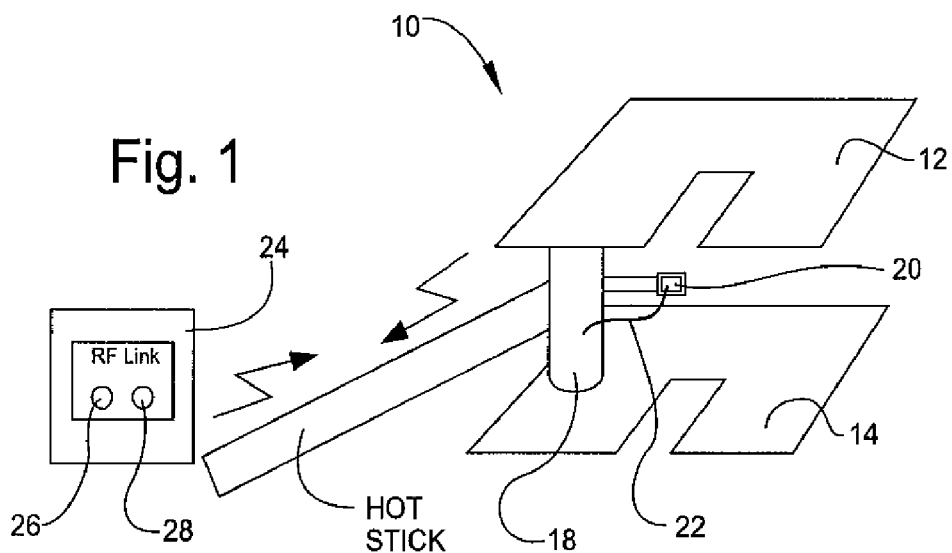
FIG. 1 is a simplified diagram of a detector according to one embodiment of the invention attached to a fiberglass hot stick.

Referring now to the drawings, one implementation of a detector according to an embodiment of the invention is shown in FIG. 1 and indicated at reference numeral 10. The detector includes two electrodes 12 and 14 energized at differing electrical potentials between which the object under test, such as a fiberglass hot stick, is placed. One or more gas gaps are placed on or close to the surface of the hot stick 16 or other object under test.

A polymer insulator, HF HV supply, optical glass fiber receiver, and RF transmitter and battery are contained in a detector module 18. The gas gap with the glass fiber receiver attached is positioned between the two electrodes 12 and 14. The light from the gas gap is transmitted to the detector which then transmits the signal to the other end of the hotstick 16 using RF. The HV supply, optical detector and RF detector are positioned next to the plates, but not between them.

In this particular iteration, the level of ionization of the gas gaps is measured/observed to determine the presence of a condition which has a high conductivity or permittivity. Measurement is by the gas gap detector 20 that measures the light intensity in the gas gap. The intensity is transmitted by the glass fiber 22 to the RF transmitter in the detector module 18, and then to a RF receiver 24 that has a "go-no go" output, for example, red and green lights 26, 28. Electronic circuitry in the detector module 18, RF receiver 24, usually on the grounded end of the hot stick 15, or in another component analyzes the light intensity and compares the intensity value against a predetermined threshold level and provides a signal to the "go-no go" output.

The level of ionization of the gas gaps can be determined by eye or a camera as well as the fiber-optic link described above.

Figures 2, 3:
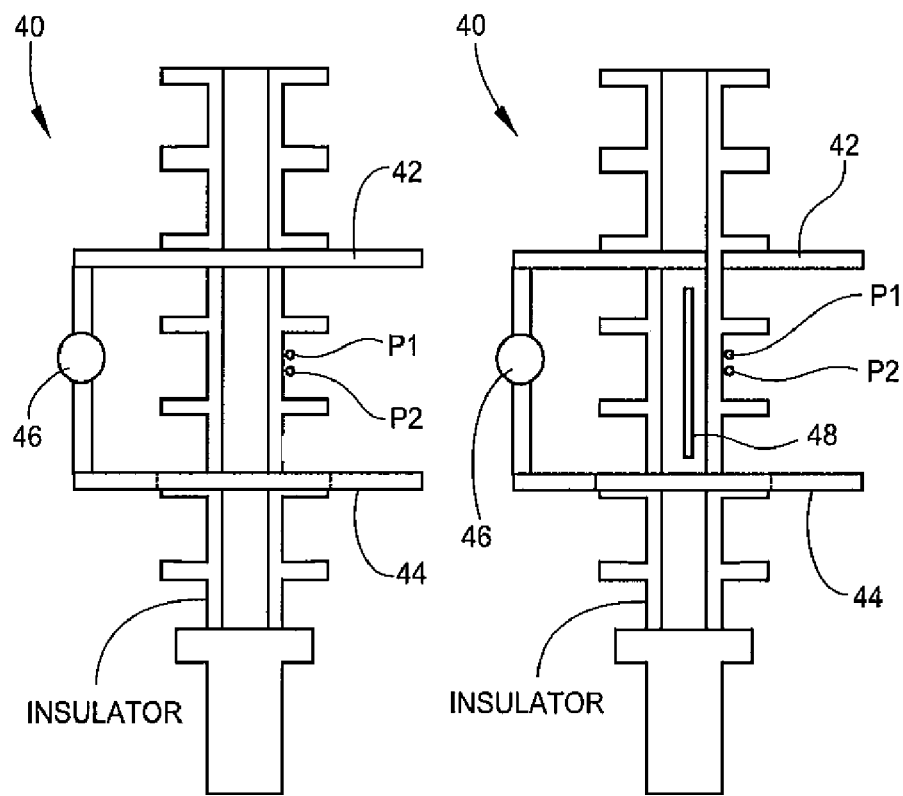
FIG. 2 is a diagram showing two electrodes surrounding a portion of an insulator.
FIG. 3 is a diagram showing two electrodes surrounding a portion of an insulator with an internal conductive object present.

Referring now to FIG. 2, a detector 40 includes two energized electrodes 42, 44 positioned on, for example, a polymer insulator, or any other insulating component with a predetermined spacing between them, as shown in FIG. 2. The voltage difference between two or more points between the electrodes 42, 44, for example P1 and P2, is then detected by a voltmeter 46 and assessed. If measured voltage difference changes significantly from the unperturbed case, i.e., the case where there is no internal/external object with high conductivity or permittivity a conductive object is concluded to be nearby.

For example, as is shown in FIG. 3, if a conductive object 48 is placed inside the insulator between the electrodes 42, 44, the change in voltage between the two points P1, P2 will be different than in the unperturbed case.

The further the measurement point is from the conductive object, the less the changes in the voltage difference between the measurement points. Therefore it is important to measure the voltage difference between the two points as close as possible to the conductive defect, i.e. as close as possible to the surface of the insulator. The location of the two voltage measurement points P1, P2 depends on the application.

Figure 4:
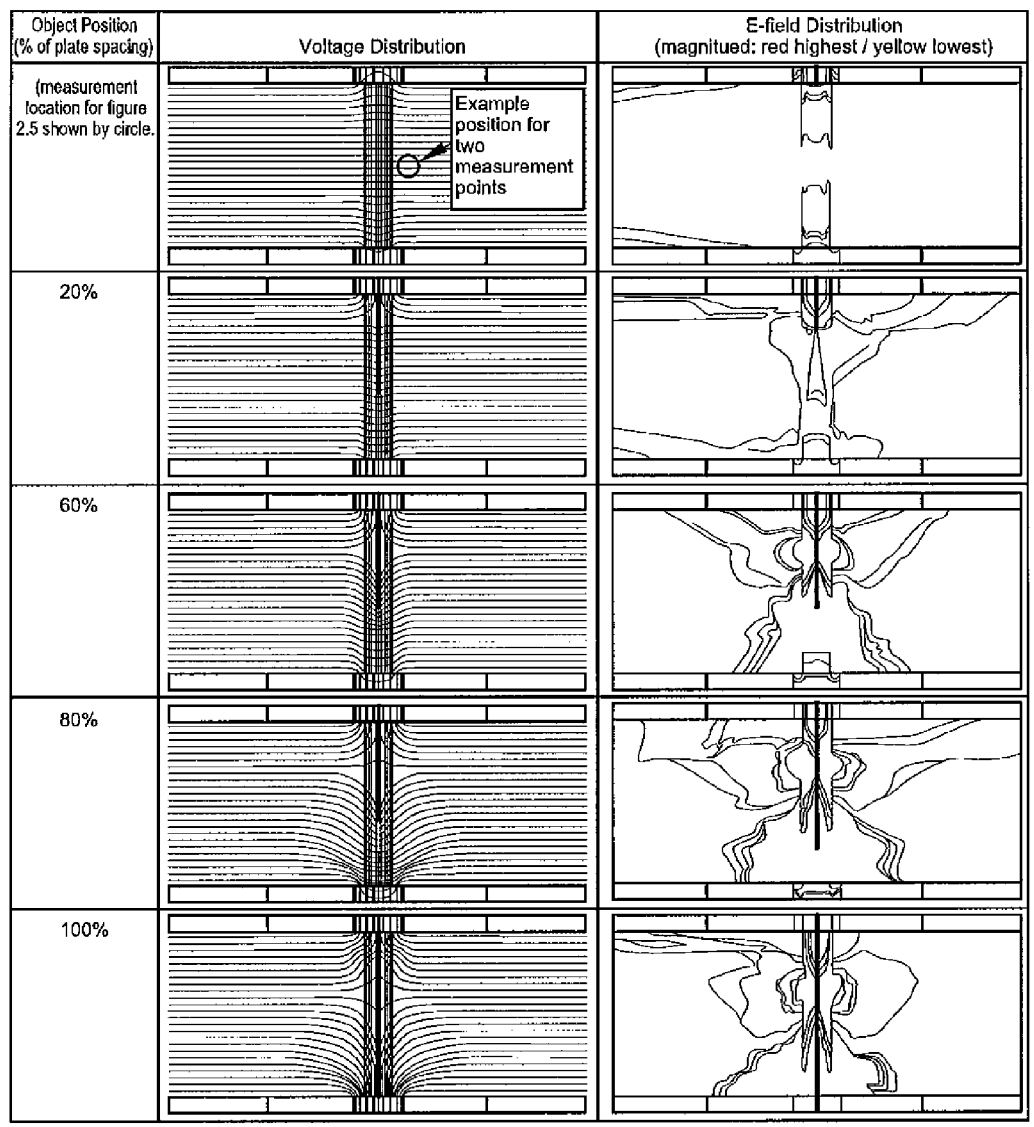
FIG. 4 is a series of tables showing the change in the voltage and E-field distribution surrounding a fiberglass rod between two electrodes as a function of conductive object position.

Referring now to FIG. 4, the tables show the change in both the voltage distribution and E-field magnitude for different positions of a conductive object, i.e., a defect, between the electrodes 42, 44. Changes in the voltage and E-field distribution surrounding a fiberglass rod, the vertically-centered structure in the voltage distribution images, between two electrodes is a function of the position of a conductive object located in the center of the fiberglass rod.

Figure 5:
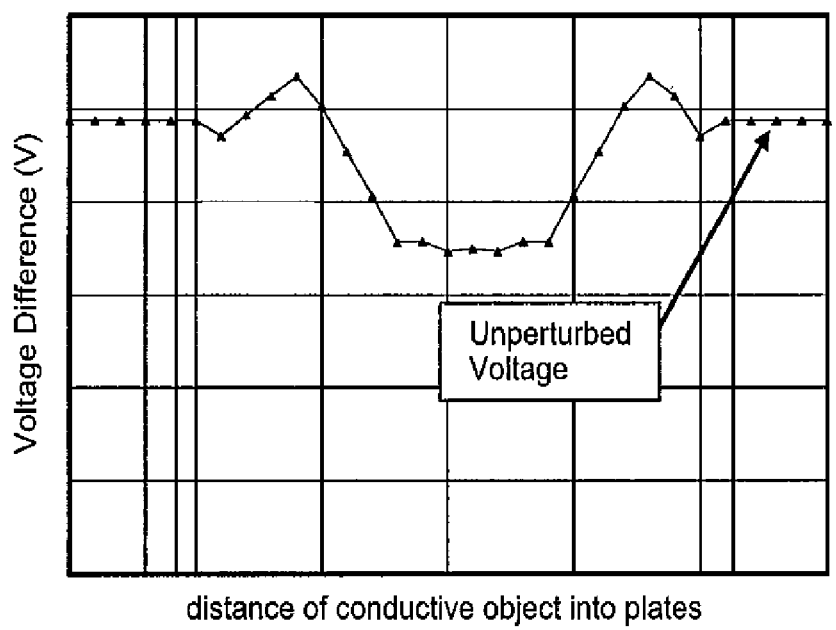
FIG. 5 is a table showing the change in the voltage difference between two points as a conductive object is moved between the plates.

Referring now to FIG. 5, a measurement of the voltage difference between two points 1 mm apart as a function of the conductive object position between the electrodes is shown. As can be seen, a change in the voltage difference compared to the unperturbed case occurs depending on the position of the conductive object. In this case the location of the measurement is halfway between the electrodes and is on the edge of the fiberglass rod insulator, as shown in FIG. 3.

Figures 6A, 6B:
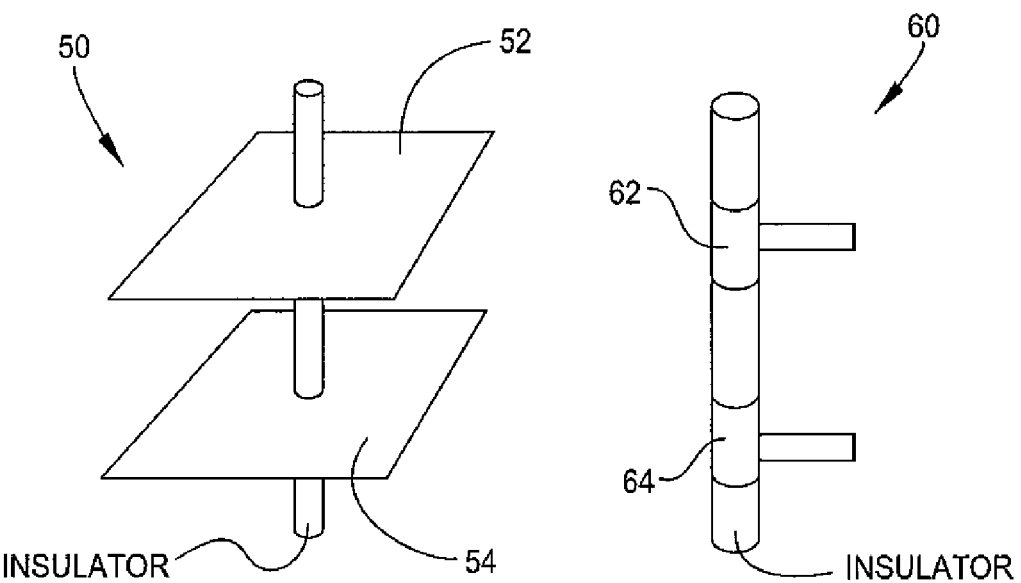
FIGS. 6A and 6B are illustrations of electrodes according to embodiments of the invention.

Although the above analysis is for a single measurement location, it may be preferable to measure at more than one location between the electrodes. This will allow a better understanding of the conductive object present and its extent. The basic principle is set up on a local electric field around a section of the object that is under test which is expected to be insulating and determine whether there is a change in the change potential or E-field distribution from what is expected. The voltage between the two different points is measured using gas gaps placed close to or on the surface of the object under test. The level of ionization of the gas gaps is proportional to the voltage difference between the gas gap electrodes. Depending on detector configuration, the level of ionization in the gas gaps will increase or decrease when conductive, semi-conductive or high permittivity conditions are nearby The energized electrodes 42, 44 are copper, but this is not critical-other electrode materials may be used. The dimensions and spacing of the electrodes 42, 44 used depends on the component being evaluated. Two examples are shown in FIGS. 6A and 6B. In FIG. 6A, a detector 50 includes electrodes 52, 54 similar to those in FIGS. 1, 2 and 3. FIG. 6B shows a detector 60 having two electrodes 62, 64 positioned concentrically on the insulator.

The detector has been demonstrated as effective with three different high voltage sources, power frequency (e.g. 50 or 60 Hz), direct current voltages, and high frequency (HF) voltages. The preferred voltage source for this application was found to be a high frequency voltage source (a voltage source of 4 to 5 MHz was used but another range of frequencies maybe applicable). The power frequency and direct current sources worked but not as successfully. Commercially available voltage sources of these types can be purchased.

The gas gaps described above are two small metal electrodes separated by a gaseous medium. This gaseous medium can be air, neon or any other gas. When a critical voltage difference is applied, either directly or indirectly, to the metal electrodes, the gas between the electrodes ionizes resulting, in among other things, emitted light. Below the critical voltage, the gas between the electrodes remains unionized. The critical voltage depends on the dimensions of the electrodes, the spacing between the electrode and the gas between the electrodes. The detector gas gaps used were the type typically used to protect electronic circuits.

One or more gas gaps are placed between the energized electrodes. Either one or both of the gas gap(s) electrodes are electrically floating. In some cases, it maybe preferable for one of the gas gap electrodes to be attached to one of the energized electrodes. The orientation of the gas gaps depends on the application and whether one wants the gas gaps to ionize when there is a defect present or when there is not a defect present.

Electronic gas gaps were selected for this application as they are physically small in dimension as hence react to small changes in electric field distribution, i.e., they are able to identify dimensionally small defects.

If one is close to the spark gap in a low light environment identifying whether the gap is firing can be done visually. For field operations, this is not possible as the gap will be a significant distance away from the operator in bright sunlight. Therefore, a fiberoptic light intensity measurement device was used to determine whether the gap is firing and with what intensity. The advantage of using the fiber optic measurement device is that it has minimal impact on the localized E-field.

The detector may be used in different modes depending on the insulating object being assessed. For the case of the polymer insulator, a short section of the insulator will be placed between the energized electrodes. The gas gap(s) will be positioned such that they are close to the surface of the insulator. If there is no internal or external defect, the gas gaps will ionize at the expected level. If, however, an electrical condition is present, then the level of ionization will change. The preferred embodiment utilizes a high frequency high voltage generator to energize two parallel electrodes with two gas gaps placed between the electrodes. The gas gaps extinguish in the presence of a conductive defect internal to a polymer insulator.

A method and apparatus for identifying the presence of high conductivity or permittivity conditions in electrically insulating materials are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. An apparatus for detecting the presence of high conductivity or permittivity conditions in electrically insulating materials, comprising:
   (a) first and second electrodes positioned proximate an insulator, the first and second electrodes being spaced-apart to define a test area therebetween;
   (b) a high voltage source connected to the first and second electrodes for energizing the first and second electrodes at different voltage potentials;
   (c) at least one gas gap device positioned in the test area, the gas gap device operable to emit a visible signal in the presence of a pre-determined voltage difference; and
   (d) a detector positioned adjacent the gas gap device to receive the visible signal from the gas gap device and generate a signal indicative of the voltage difference.

2. An apparatus according to claim 1, wherein the high voltage source is selected from the group of high voltage sources consisting of a high frequency, high voltage source, a direct current source and a power frequency source.

3. An apparatus according to claim 1, and including a pair of closely spaced-apart gas gap devices positioned on the insulator.

4. An apparatus according to claim 1, wherein the first electrode and second electrode each comprises a plate with respective major surfaces for being positioned generally perpendicular to a longitudinal axis of the insulator being tested.

5. An apparatus according to claim 1, and including a detector module having a receiver for receiving data indicative of the voltage difference from the detector and a transmitter for transmitting the data to an electronic circuit for data analysis.

6. An apparatus according to claim 5, wherein the detector comprises an optical detector for transmitting an optical signal to the receiver of the detector module.

7. An apparatus according to claim 1, and including an RF transmitter for transmitting data indicative of the voltage difference to an RF receiver, and an electronic circuit for analyzing the data and comparing the data against a predetermined threshold level and providing an output value.

8. An apparatus for detecting the presence of high conductivity or permittivity conditions in electrically insulating materials, comprising:

(a) a first electrode plate and a second electrode plate positioned proximate an insulator, the first and second electrode plates being spaced-apart to define a test area therebetween;

(b) a HF HV source connected to the first and second electrode plates for energizing the first and second electrode plates at different voltage potentials such that a localized electric field is formed therebetween;

(c) first and second gas gap devices positioned in spaced-apart relation in the test area, the first and second gas gap devices being operable to emit a visible signal in the presence of a pre-determined level of ionization indicating a disturbance in the electric field;

(d) an optical detector positioned adjacent the first and second gas gap devices to receive the visible signal and generate a data signal indicative of the level of ionization; and (e) a detector module having a receiver for receiving the data signal from the optical detector and an RF transmitter for transmitting the data signal to an RF receiver of an electronic circuit, wherein the electronic circuit compares the data signal against a predetermined threshold level and provides an output value.

9. A method for detecting the presence of high conductivity or permittivity conditions in electrically insulating materials, comprising the steps of:

(a) positioning a first electrode and a second electrode in spaced-apart relation to an insulator such that a test area is formed therebetween;

(b) positioning at least one gas gap device in the test area formed between the first electrode and the second electrode and proximate a surface of the insulator;

(c) energizing the first electrode and second electrode with a high voltage source at different potentials; and (d) detecting the level of ionization of the at least one gas gap device while the electrodes are energized.

10. A method according to claim 9, wherein the method of energizing the first and second electrodes with the high voltage source comprises the step of applying a high voltage from the group of high voltage sources consisting of a high frequency, high voltage source, a direct current source and a power frequency source.

11. A method according to claim 9, and including the step of positioning a pair of closely spaced-apart gas gap devices between the first electrode and the second electrode.

12. A method according to claim 9, wherein the first and second electrodes each include plates having opposed major surfaces, and including the step of positioning the first and second electrode plates with their respective major surfaces generally perpendicular to a longitudinal axis of the insulator being tested.

13. A method according to claim 9, and including the step of receiving data indicative of the level of ionization from a detector and transmitting the data to an electronic circuit for data analysis.

14. A method according to claim 9, wherein the step of detecting the level of ionization comprises detecting light indicative of the level of ionization with an optical detector and transmitting the optical signal to a receiver.

15. A method according to claim 14, and including the steps of providing a RF transmitter for transmitting data indicative of the level of ionization of the at least one gas gap device while the electrodes are energized to a RF receiver, and utilizing an electronic circuit for analyzing the data and comparing the data against a predetermined threshold level and providing an output value.

16. A method for detecting the presence of high conductivity or permittivity conditions in electrically insulating materials, comprising:

(a) providing a first electrode plate and a second electrode plate positioned proximate an insulator and spaced-apart to define a test area therebetween;

(b) providing a HF HV source for energizing the first electrode and second electrode at different potentials;

(c) positioning first and second gas devices in spaced-apart relation between the first electrode and the second electrode proximate a surface of the insulator;

(d) energizing the first electrode and second electrode at different potentials;

(e) utilizing an optical detector to determine the level of ionization of the first and second gas devices while the electrodes are energized;

(f) detecting data indicative of the level of ionization and transmitting the data to an electronic circuit for data analysis; and (g) analyzing the data and comparing the data against a predetermined threshold level and providing an output value.

* * * * *